United States Patent
Karlsen et al.

(10) Patent No.: US 10,264,373 B2
(45) Date of Patent: Apr. 16, 2019

(54) HEARING AID COMPRISING A LOCKING MECHANISM

(71) Applicant: Oticon Medical A/S, Smørum (DK)

(72) Inventors: Morten Friis Karlsen, Smørum (DK); Claus Tipsmark, Smørum (DK)

(73) Assignee: OTICON MEDICAL A/S, Smørum (DK)

( * ) Notice: Subject to any disclaimer, the term of this patent is extended or adjusted under 35 U.S.C. 154(b) by 0 days.

(21) Appl. No.: 15/644,399

(22) Filed: Jul. 7, 2017

(65) Prior Publication Data
US 2018/0014132 A1 Jan. 11, 2018

(30) Foreign Application Priority Data
Jul. 8, 2016 (EP) .................. 16178631.4

(51) Int. Cl.
*A61N 1/36* (2006.01)
*H04M 1/62* (2006.01)
*H04R 1/10* (2006.01)
*H04R 25/00* (2006.01)

(52) U.S. Cl.
CPC ............ *H04R 25/602* (2013.01); *H04M 1/62* (2013.01); *H04R 1/1058* (2013.01); *H04R 25/60* (2013.01); *H04R 25/608* (2013.01); *H04R 25/65* (2013.01); *A61N 1/36038* (2017.08); *H04R 2225/61* (2013.01)

(58) Field of Classification Search
CPC ....... H04R 25/60; H04R 25/602; H04R 25/65
USPC .................................................. 381/322–324
See application file for complete search history.

(56) References Cited

U.S. PATENT DOCUMENTS

| 6,625,290 | B1* | 9/2003 | Dittli ............... H04R 25/60 381/322 |
| 7,715,582 | B2* | 5/2010 | Ochsenbein ......... H04R 25/604 381/322 |
| 10,104,481 | B2* | 10/2018 | Crook ................. H04R 25/602 |
| 2003/0156727 | A1 | 8/2003 | Vonlanthen |
| 2009/0041277 | A1 | 2/2009 | Kral et al. |
| 2011/0211718 | A1* | 9/2011 | Chua ................... H04R 25/602 381/323 |
| 2014/0328492 | A1 | 11/2014 | Feeley et al. |
| 2017/0142531 | A1* | 5/2017 | Crook ................. H04R 25/602 |

* cited by examiner

*Primary Examiner* — Jesse A Elbin
(74) *Attorney, Agent, or Firm* — Birch, Stewart, Kolasch & Birch, LLP

(57) ABSTRACT

According to an embodiment, a hearing aid is disclosed. The hearing aid includes a first functional unit and a second functional unit. The second functional unit is configured to removably couple with the first functional unit. The coupling provides at least a mechanical connection between the first functional unit and the second functional unit. The first functional unit includes a moveable element that is configured to move between a first position and a second position. In the first position, the moveable element is contained entirely within the first functional unit. In the second position, a part of the moveable element is configured to protrude out of the first functional unit. The second functional unit includes a recess configured to receive the part of the moveable element that protrudes out of the first functional unit such that the first functional unit and the second functional unit are immovably locked with respect to each other in response to the moveable element is received in the recess.

19 Claims, 8 Drawing Sheets

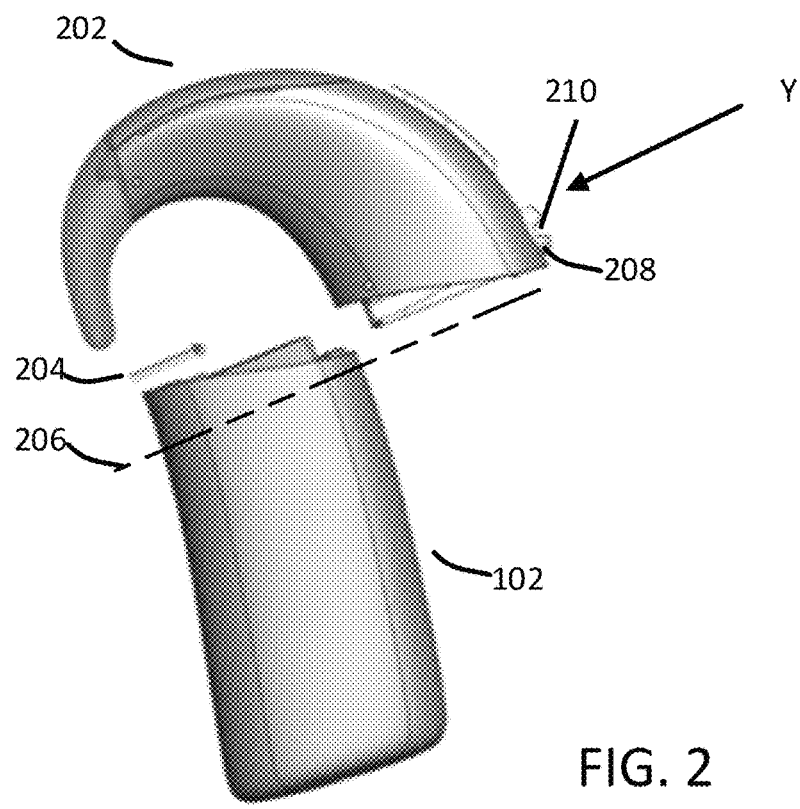
FIG. 2
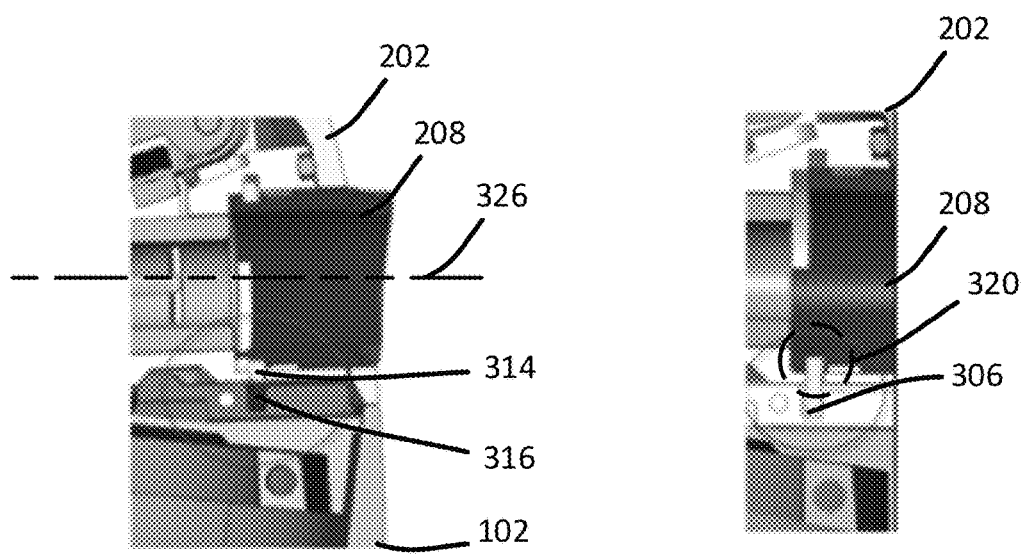
FIG. 3C
FIG. 3D

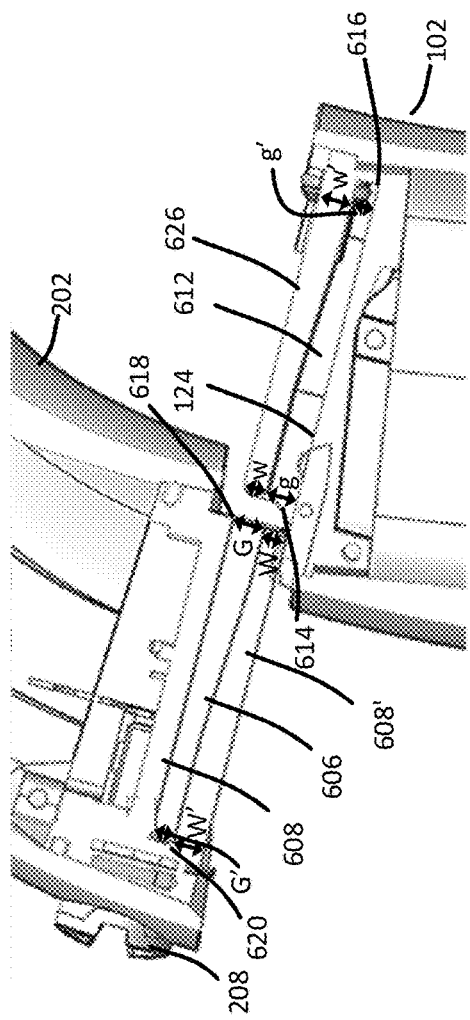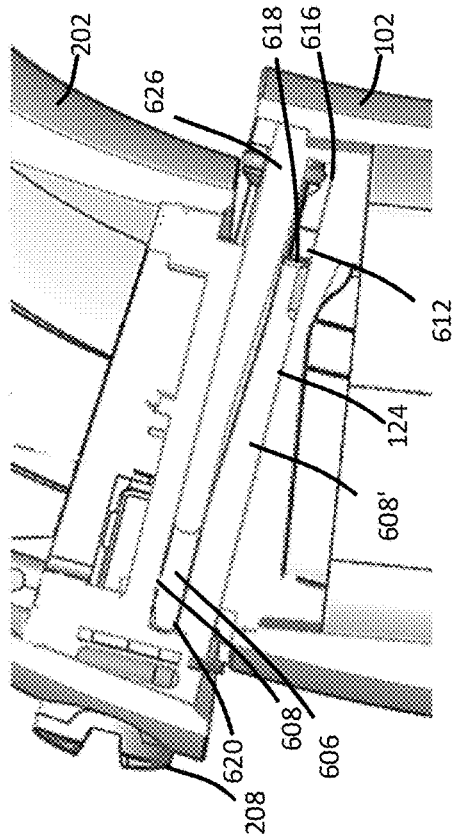

HEARING AID COMPRISING A LOCKING MECHANISM

FIELD

The disclosure relates to a locking mechanism. In particular, the disclosure relates to a hearing aid comprising the locking mechanism that allows for locking a first functional unit and a second functional unit of the hearing aid, wherein the first functional unit and the second functional unit are removably coupled. One such example includes the first functional unit such as a housing comprising electronics and the second functional unit such as a battery compartment including a battery.

BACKGROUND

A hearing aid is a hearing device for aiding an individual in regard to his or her hearing. It may be a hearing prosthesis for compensating a hearing loss, namely a conventional acoustic hearing aid amplifying sound or a cochlear implant electrically stimulating nerve cells or a bone conduction hearing aid. It may also be a hearing protection device which helps individuals to hear without damage in noisy environments. It may also be a tinnitus treatment device. The individual may be an adult, but it may also be an infant or child.

Commercially available electrical hearing aids include a battery compartment for holding a battery. The battery compartment for hearing aids may be constructed in various ways. One common way is to construct the battery compartment as a drawer or a holder, in which the battery is placed, upon which the drawer is pushed around a pivot point from an open position into a closed position in the housing. In this way, the housing serves to close the battery compartment. Typically the holder has a pivot point about which the holder rotates while being pushed into the housing. Retaining means may be provided to hold the battery compartment in the closed position, and possibly in an intermediate position where the power supply to the hearing aid is interrupted but the battery is not accessible for removal.

The battery compartment generally requires the hearing aid users such as elderly people to perform the delicate manipulations of applying pivoting force on the drawer, for example to detach the battery compartment. In order to prevent the battery compartment from being opened accidently, and the battery thus falling out, the battery compartment is locked in the housing by a locking mechanism. For example, if the user is an infant, it may be important to lock the battery compartment such that the battery cannot be removed and possibly swallowed. Such hearing aid devices may be referred to as childproof, tamperproof.

The disclosure provides an alternative solution to the above-described situation by offering a locking mechanism between the first functional unit and the second functional unit of the hearing aid such that coupling of the first functional unit and the second functional unit is provided with immovable locking using the locking mechanism.

SUMMARY OF THE INVENTION

According to an embodiment, a hearing aid includes a device that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. Such audible signals may be provided in the form of an acoustic signal impinged on the ear drum of the user such as in traditional hearing aid, or an acoustic signal transferred as mechanical vibrations to the user's inner ears through bone structure of the user's head such as in bone conduction hearing aid and/or through parts of middle ear of the user such as in middle ear implants or electric signals transferred directly or indirectly to cochlear nerve such as in cochlear implants and/or to brainstem of the user such as in auditory brainstem implants.

The implementation presented in the disclosure may also be applied generally in other hearing devices. Therefore, for such situation, the hearing aid may also refer to a device such as an earphone or a headset adapted to receive an audio signal electronically, possibly modifying the audio signal and providing the possibly modified audio signals as an audible signal to at least one of the user's ears typically by way of acoustic signals to the ear drum.

The hearing aid is adapted to be worn in any known way. This may include i) arranging a unit of the hearing device behind the ear with a tube leading air-borne acoustic signals into the ear canal or with a receiver/loudspeaker arranged close to or in the ear canal such as in a Behind-the-Ear type hearing aid, and/or ii) arranging a unit of the hearing device behind the ear with a wire leading electrical signals to a transmitter coil adapted to transmit the electrical signals to an implantable receiver coil, such as Behind-the-Ear type speech processor of a cochlear implant, and/or iii) arranging a unit of the hearing device attached to a fixture implanted into the skull bone such as in Bone Anchored Hearing Aid.

A "hearing system" refers to a system comprising one or two hearing devices, and a "binaural hearing system" refers to a system comprising two hearing aids where the aids are adapted to cooperatively provide audible signals to both of the user's ears. The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone such as with an mobile app or other electronic device, the SmartPhone/electronic device possibly running an application that controls functionality of the at least one hearing device.

According to an embodiment, the hearing aid includes a first functional unit and a second functional unit. One of the first functional unit or second functional unit may include a housing comprising an electronic component such as an input unit including a microphone, and/or signal processing unit. Another of the first functional unit or second functional unit may be selected from a battery compartment including battery, FM receiver, audio shoe, or other accessory unit. The skilled person would appreciate that the components contained in the first functional unit and the second functional unit may include different configurations and the disclosure is not limited to a specific configuration. For example, the disclosure is described with the first functional unit comprising a microphone and a signal processing unit whereas the second functional unit is a battery compartment including a battery that provides the first functional unit with energy. In other possible configurations, the first functional unit may include only the microphone whereas the second functional unit may include the signal processing unit, battery and a speaker. In different embodiments, the first functional unit and the second functional unit are at least mechanically coupled. Additionally, the first functional unit and the second functional unit are electrically coupled to each other, i.e. the at least one component of the first functional unit and at least one component of the second functional unit are electrically connected to each other.

In an embodiment, the first functional unit is selected from a speech processor of a cochlear implant and behind the ear hearing aid and the second functional unit is a battery compartment. In another embodiment, the first functional unit is a speech processor of a cochlear implant and behind the ear hearing aid and the second functional unit is an accessory unit for the cochlear implant and behind the ear hearing aid respectively.

Having different components in removably coupled functional units allows for including additional functionalities to the hearing aid by way of coupling a functional unit providing desired functionality to the functional unit comprising the signal processing unit. Such configuration also allows for replacing only the functional unit comprising a faulty component rather than the entire hearing aid. Thus, not only the cost of maintenance is reduced but also the hearing aid may be used continuously for assisting the hearing impaired if the faulty functional unit is other than the one that provides basic function of the hearing aid, i.e. improving hearing capability of the hearing aid user.

In an illustrative embodiment, the hearing aid includes
a) a first functional unit i) includes an input unit such as a microphone for receiving an acoustic signal from a user's surroundings and providing a corresponding input audio signal and/or ii) a receiving unit for electronically receiving an input audio signal. The first functional unit further includes a signal processing unit for processing the input audio signal and an output unit for providing an audible signal to the user in dependence on the processed audio signal.

b) a second functional unit comprising a battery compartment including at least one battery. The second functional unit is configured to removably couple with the first functional unit.

According to an embodiment, the hearing aid includes a battery compartment comprising a battery chamber and a chamber cover. The battery chamber is configured to hold the battery and is adapted to slide into the battery chamber along a guide rail in an axial direction. The battery chamber includes a cut out section provided at an external surface of the battery chamber. The cut out section is adapted to receive a corresponding cut out element of a rotatable screw for locking the battery chamber with the chamber cover. In the locked state, the battery chamber and chamber cover cannot be separated along the axial direction. That is, the rotatable screw needs to be manipulated before the locked state is changed to unlocked state and the battery chamber can be withdrawn from the chamber cover.

Additionally or alternatively, one of the guide chamber and chamber cover includes a hole whereas another of the guide chamber and chamber cover includes a projected piece that snap locks in to the hole when the battery chamber is completely received in the chamber cover. This provides a snap-locking resistance against withdrawing of the battery chamber from battery compartment. Additionally or alternatively, one of the guide chamber and chamber cover includes a first magnet whereas another of the guide chamber and chamber cover includes a second magnet of opposite polarity. The first magnet and second magnet are adapted to cooperate when the battery chamber is completely received in the chamber cover. This provides a magnetic resistance against withdrawing of the battery chamber from battery compartment. Furthermore, these embodiments also indicate complete insertion of the battery chamber in the chamber cover, thereby indicating that the locking using the rotatable screw can be initiated.

In an embodiment, the chamber cover may include a through-going hole that is adapted to allow insertion of the rotatable screw such that the rotatable screw is accessible for rotation from outside of the battery cover whereas the cut out element is rotatable within the battery cover when a rotational force on the rotatable screw is applied.

The chamber cover may include a one piece assembly with a single opening from where the battery chamber is inserted in an axial direction. Typically, the axial direction may run along the longest side of the chamber cover.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. Additionally or alternatively, in case of cochlear implant system such amplification may be provided by frequency specific acoustic level—electrical charge mapping as described in U.S. patent application Ser. No. 14/328,228 (see FIG. 3). The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

According to an embodiment, a hearing aid is disclosed. The hearing aid includes a first functional unit and a second functional unit. The second functional unit is configured to removably couple with the first functional unit. The coupling may be defined as providing at least a mechanical connection between the first functional unit and the second functional unit. The first functional unit includes a moveable element that is configured to move between a first position and a second position. In the first position, the moveable element is contained entirely within the first functional unit. In the second position, a part of the moveable element is configured to protrude out of the first functional unit. The second functional unit includes a recess configured to receive the part of the moveable element that protrudes out of the first functional unit such that the first functional unit and the second functional unit are immovably locked with respect to each other in response to the moveable element is received in the recess. Such locking is along a translation axis.

The term "removably couple" means that the first functional unit and the second functional unit are mechanically connectable to each other but the two units may be detached by application of a force (detaching force) of a specific magnitude on one of the functional units relative to the another functional unit in a predefined direction, as defined by a translation axis.

The term "contained entirely" means that the moveable element is configured to be enclosed within a body of the first functional unit without any part of the moveable element extending out of the body, i.e. the moveable element is invisible when entirely contained within the body. The "contained entirely" may also mean that the moveable part is enclosed within the body while a part of the moveable part extends out of the body of the first functional unit. However, the part extending out of the body is configured to be prevented from being received in the recess of the second functional unit. Such prevention may be achieved by having an optimum dimension of the part such that the part is prevented from being received in the recess.

The term "first position" is defined by position of the moveable element when the moveable element is contained entirely within the first functional unit and/or is prevented from being received by the recess. In the first position, the first functional unit and the second functional unit are prevented from being immovably locked with one another. In the first position, the first functional unit and the second functional unit are either not mechanically coupled to each other or if mechanically coupled, the first functional unit and the second functional unit may be detached by application of the force (detaching force) of specific magnitude on one of the functional units relative to another functional unit in the predefined direction (translation axis).

A hearing aid where the moveable element is contained entirely within the first functional unit allows for providing a discreet locking solution. This allows for a) providing a solution that is aesthetically pleasing, b) protects the locking mechanism from wear and tear from external environment, and c) hides the locking mechanism from children who may have a tendency to fiddle with the mechanism.

The term "second position" is defined by the position of the moveable element when the part of the moveable element protruding out of the first functional unit is received by the recess of the second functional unit. The moveable element may be configured to protrude out in response to an actuation force. In the second position, the first functional unit and the second functional unit are immovably locked with respect to each other. In the second position, the moveable element is preferably contained partially within the first functional unit and partially within the second functional unit such that the moveable element is contained entirely within the first functional unit and the second functional unit in combination. Thus, the moveable element is configured to be invisible even in the second position.

A hearing aid where the moveable element is contained entirely within the first functional unit and the second functional unit in combination also allows for providing a discreet locking solution. This allows for a) providing a solution that is aesthetically pleasing, b) protects the locking mechanism from wear and tear from external environment, and c) hides the locking mechanism from children who may have a tendency to fiddle with the mechanism.

The term "immovably locked" means that that first functional unit and the second functional unit are prevented from being detached even when the force (detaching force) of a specific magnitude is applied on one of the functional units relative to another functional unit is applied in the predefined direction, as defined by a translation axis.

A hearing aid where the first functional unit and the second functional unit are immovable locked in the second position allows for providing a reliable childproof or tamperproof locking mechanism because even an accidental or intentional application of the force (detaching force) of the specific magnitude on one of the functional units relative to another functional unit in the predefined direction (translation axis) would not detach the two functional units unless the moveable element is moved back to the first position prior to the application of the detaching force.

Thus, the hearing aid where the first functional unit and the second functional unit are immovably locked, in accordance with the disclosure, provides an alternative way of reliable childproof or tamperproof locking mechanism.

According to an embodiment, the moveable part is coupled to an actuator, at least partly comprised in the first functional unit and accessible from outside a body of the first functional unit. The actuator is configured to move the moveable element between the first position and the second position. The actuator may be manually controlled preferably using an actuator tool.

The first functional element may include a groove along which the moveable element and/or the actuator moves. Typically the actuator moves along the groove and its coupling with the moveable element makes the moveable element to move in accordance with a path defined by the groove. In one embodiment, the moveable element comprises a rotatable unit and the groove includes a circular or partially circular groove around a rotation axis and including the slit as part of the circular or partially circular groove. The actuator may be moved 90 degrees for moving the rotatable unit between the first position and the second position. In another embodiment, the moveable element includes a slidable unit and the groove includes a pair of opposite grooves along a slide axis and including the slit as part of the pair of opposite grooves.

In an embodiment, the actuator includes an engagement element that is configured to engage with the actuator tool. In an engaged arrangement, the actuator tool engages with the engagement element, wherein the actuator tool may be configured to move the actuator such that the actuator may move the moveable element between the first position and the second position.

In different configurations, the engagement element may include a) a surface depression to receive an end of the actuator tool similar to a screw head, and/or b) a pair of indentations at a periphery of the actuator that are configured to receive complimentary shaped end of the actuator tool. The indentation may include a U-shaped notch or V-shaped notch and the complimentary shaped end may include a flat blade (like a flat bladed screwdriver head) or a U-shaped cut or V-shaped cut that are configured to engage with the -shaped notch or V-shaped notch respectively such that the vertices of the Us (for U-shaped notch-cut) or Vs (for V-shaped notch-cut) are configured to abut each other for moving the actuator for example in a rotational direction around a rotational axis.

In an embodiment where the hearing aid is a speech processor of a cochlear implant, the actuator may comprise an antenna cable output port adapted to connect the speech processor with a transmitter unit using an antenna cable. The transmitter unit is configured to receive the audio electrical signals from the speech processor and to transmit the received audio electrical signal to an implantable receiver unit. The actuator may thus include a through hole such that the antenna cable is configured to connect to a connector comprised within the first functional unit, the connector being configured to provide electrical connection with the electronics such as the signal processing unit comprised within the first functional unit.

In an embodiment, the positioning of the actuator within the first functional unit is configured to provide a locking between the connector (of the preceding paragraph) and a body of the first functional unit. In typical set up, locking between the connector and Such locking between the connector and the body is typically provided with a pin. However, in the disclosed embodiment, the actuator is configured to provide the functionality of the pin for the locking. This allows for optimal utilization of otherwise limited volumetric space of the first functional unit, whereby the actuator is configured to not only perform the function of providing actuation force to lock the first functional unit with the second functional unit but also provide locking of the connector with the body of the first functional unit.

The actuator is at least partly comprised in the first functional unit. In an embodiment, the actuator is fully comprised within the first functional unit. The periphery of the actuator is preferably flush with the outer surface of the body of the first functional unit.

The skilled person would appreciate that different embodiments of the disclosure are combinable. For example, the actuator that is partly comprised or fully comprised in the first functional unit may comprise the antenna cable output port.

Having the actuator completely comprised in the first functional unit allows for a) providing a solution that is aesthetically pleasing, b) protects the locking mechanism, in particular the actuator from wear and tear from external environment, and c) hides the locking mechanism from children who may have a tendency to fiddle with the mechanism.

Having the actuator comprising the antenna cable output port allows for a) providing a dual purpose solution, thus effectively using space in typically size constrained hearing aid, b) surreptitiously hiding the locking mechanism from children who may have a tendency to fiddle with the mechanism.

Having the actuator comprising the antenna cable output port and a periphery flush with the outer surface of the body of the first functional unit allows for a) providing a dual purpose solution, thus effectively using space in typically size constrained hearing aid, b) surreptitiously hiding the locking mechanism from children who may have a tendency to fiddle with the mechanism, c) protecting the locking mechanism, in particular the actuator from wear and tear from external environment, and d) providing protection to the antenna cable within the first functional unit until the cable reaches surface of the body of the first functional unit.

The first functional part may further include a slit configured to allow the part of the moveable element to protrude out of the first functional unit in response to an actuation force applied to the actuator. The actuation force may be understood as the minimum force required to move the moveable element between the first position and the second position. In accordance with the implementation, the actuation force may include a force along a straight (slide) axis and/or a torque around a rotation axis. In a preferred embodiment, the slit is adapted to be invisible when the first functional unit and the second functional unit are immovably locked with respect to each other.

According to an embodiment, the hearing aid includes a friction element arranged within the first functional unit, the friction element being configured to cooperate with the moveable element and/or actuator such that the moveable element moves between the first position and the second position in response to the actuation force that is above a friction threshold, which defined by the friction between the friction element and moveable element and/or actuator. The feature allows for requiring an increased actuation force for moving the moveable element between the first position and second position, thus avoiding accidental movement of the moveable element between the two positions and unintentional unlocking of the first function unit and the second functional unit. In one embodiment, the moveable material comprises a moveable periphery abutting the friction element and/or actuator comprising a actuator periphery abutting the friction element, the moveable periphery and/or actuator periphery being configured to apply compression force against the friction element, defining cooperation, when the moveable material moves between the first position and the second position. Additionally or alternatively, the moveable element comprises a surface abutting the friction element, the surface being configured to apply the compression force against the friction element, defining cooperation, when the moveable element moves between the first position and the second position. In these embodiments, the friction threshold is defined by the force required to overcome the friction between the periphery and the friction element and/or surface and the friction element in order to move the moveable element between the first position and the second position. In an embodiment, the friction element is made of a compressible material such as hard or soft rubber or thermoplastic material such as Polyether ether ketone (PEEK) or Polyoxymethylene (POM). In a combinable embodiment, the friction element is configured to cooperate with the moveable element and/or actuator only between the first position and the second position. In other words, the friction element is configured to prevent cooperation with the moveable element when the moveable element is at the first position and at the second position.

In an embodiment, the friction element is positioned within the first functional unit such that a clearance is provided between the friction element and adjacent component, the clearance being configured to accommodate the flex induced in the friction element because of the compression force applied by the moveable element and/or actuator.

In one embodiment, the friction element comprises at least one pair of friction sub-elements that are positioned on same end or opposite end of the periphery of the moveable element or actuator. In another embodiment, the friction element comprises at least one pair of friction sub-elements that are positioned on same side or opposite sides of the surface of the moveable element. In either embodiment, providing a pair of oppositely positioned friction sub-elements ensures that the advantages of the friction element are at least partially retained even if one of the sub-element becomes faulty or fails due to over use or aging.

According to an embodiment, the moveable element comprises a rotatable unit configured to rotate around a rotation axis. The actuator may include a rotatable actuator configured to rotate around the rotation axis, the rotation of the actuator is configured to rotate the rotatable unit around the rotation axis between the first position and second position. The rotation of the actuator may be achieved by applying a rotational force (torque) on the actuator that in turn rotates the rotatable unit such that a part of the rotatable unit protrudes out of the slit and is received in the recess of the second functional unit. In an embodiment, the rotation axis is defined by an axis that is generally parallel to a first surface and a second surface of the first functional unit and the second functional unit respectively.

According to an embodiment, the rotatable unit includes a primary section defining the part that is adapted to protrude out of the first functional unit and a secondary section. A primary distance defines a distance between the rotation axis and an outer periphery of the primary section, The primary distance is more than a secondary distance defining a distance between the rotation axis and an outer periphery of the secondary section. During rotation of the rotatable unit, the primary section protrudes out of the slit and when the rotatable unit reaches the second position, at least a part of the primary section is received in the recess of the second functional unit.

According to an embodiment, the rotatable unit comprises the primary section, the secondary section and a peripheral gap. The peripheral gap is provided between the primary section and the secondary section or between a first part and a second part of a dual-part secondary section. The peripheral gap may be defined by an at least partial cut out section in the surface of the rotatable unit. The peripheral gap may be useful in providing a force stop at the first position and the second position, thus allowing the user to know precisely when the first position and the second position is reached.

According to an embodiment, in the first position, the peripheral gap is configured to face the slit or the outer periphery of the primary section is configured to remain within the first functional unit and the outer periphery of the secondary section is configured to face the slit while remaining within the first functional unit with or without at least a section of the outer periphery of the secondary section being flush with the slit. In the second position, the outer periphery of the primary section is configured to protrude out of the slit and the outer periphery of the secondary section and/or peripheral gap is configured to remain within the first functional unit.

According to an embodiment, the first functional unit comprises a stop member configured to functionally couple to the actuator and/or rotatable unit for limiting rotation of the actuator and/or rotatable unit at at least one of the first position and the second position. The stop member may include a stoppage along the groove such that rotation of the moveable element and/or actuator is stopped at least at the first position or second position. This may be implemented either by interaction between the stop member and at least one of the ends of the peripheral gap. This may further be implemented by interaction between the stop member and at least one extended projection of the actuator wherein the extended projection includes a peripheral extension or cut out section defining the extension at surface of the actuator, the extension or cut out section being configured to interact with the stop member at least at the first position or the second position.

According to an embodiment, the moveable element includes a slidable unit configured to slide along a slide axis. The slide axis may be perpendicular to the first surface and second surface of the first functional unit and the second functional unit respectively. The slidable unit includes a first end and a second end. The actuator may include a slidable actuator configured to slide along the slide axis, the sliding of the actual is configured to slide the slidable unit along the slide axis between the first position and second position.

In an embodiment, in the first position, a first edge of the first end is configured to face the slit while remaining within the first functional unit with or without being flush with the slit; and in the second position, the first edge of the first end is configured to protrude out of the slit and a second edge of the second end is configured to remain within the first functional unit. In an embodiment, the slidable unit comprises a surface between the first end and the second end, the surface being defined by the primary surface and a secondary surface. In the first position, the surface is contained entirely within the first functional unit, whereas in the second position, the primary surface including the first edge is configured to protrude out of the slit and received within the recess and the second surface including the second edge is retained within the first functional unit.

According to an embodiment, the first functional unit comprises a first surface comprising the slit and the second functional unit comprises a second surface comprising the recess. The first surface and the second surface are configured to abut surfacially when the first functional unit and the second functional unit are arranged immovably with respect to each other.

According to an embodiment, the slit of the first functional unit is configured to align with the recess of the second functional unit when the first functional unit and the second functional unit are positioned in the immovably locked position.

According to an embodiment, the first functional unit comprises a first pair of at least substantially parallel sides, each comprising a first guide channel defined by a first gap between a pair of extension portions of the side. The second functional unit includes a second pair of at least substantially parallel sides, each comprising a second guide channel defined by a second gap between the second surface and a second extension portion of the side. One of the pair of extension portions is adapted to slide between a second receiving edge of the second surface though the second guide channel to a second terminating end of the second surface and the second extension portion is adapted to slide between a first receiving edge of the first surface though the first guide channel to a first terminating end of the first surface. The skilled person would appreciate that in other embodiment, the arrangement of the extensions may be reversed, that is the first guide channel is defined by a gap between the first surface and an extension portion, whereas the second guide channel is defined by a pair of extension portions.

The sliding motion of the first extension portion and the second extension portion is along the translation axis, which may also run parallel to the first surface of the first functional unit and the second surface of the second functional unit.

In an embodiment, the first extension portion and the second extension portion extends in opposite directions. For example, the first extension portion may extend outwards whereas the second extension portion may extend inwards. Alternatively, the first extension portion may extend inwards whereas the second extension portion may extend outwards. The term inwards or outwards refers to facing towards or away from the recess and/or slit.

In an embodiment, the first pair of the at least substantially parallel sides are separated by a first distance defining a width of the first surface. In an embodiment, the second pair of the at least substantially parallel sides are separated by a second distance defining a width of the second surface. In an embodiment, the first pair of the at least substantially parallel sides run along the entire length or substantially the entire length of the first surface. In an embodiment, the second pair of the at least substantially parallel sides run along the entire length or substantially the entire length of the second surface. The skilled person would appreciate that these recited embodiments are combinable with one another.

The first receiving edge is defined by a first open section, adjacent to the first guide channel, where the second projection enters the first guide channel such that the first functional unit and the second functional unit become moveable to achieve a coupled position. Similarly, the second receiving edge is defined by a second open section, adjacent to the second guide channel, where the first projection enters the second guide channel such that the first functional unit and the second functional unit become moveable to achieve the coupled position.

The first terminating end is defined by a first blocked section, adjacent to the first guide channel, where movement of the second projection along the first guide channel is blocked when the second projection is moved along the translation axis. Similarly, the second terminating end is defined by a second blocked section, adjacent to the second guide channel, where movement of the first projection along the second guide channel is blocked when the first projection is moved along the translation axis.

In an embodiment, the first pair of substantially parallel sides are at least substantially perpendicular to the first surface and the second pair of at least substantially parallel sides are at least substantially perpendicular to the second surface.

Having the first guide channel configured to allow sliding of the second extension portion and the second channel configured to allow sliding of the first extension portion allow for a more reliable sliding motion while coupling the first functional unit with the second functional unit.

According to an embodiment, the hearing aid includes the first gap that is configured to decrease in a first gap width starting from a first receiving edge to a first terminating end; and the second gap is configured to decrease in a second gap width starting from a second receiving edge to a second terminating end. The hearing aid further includes one of the extension member of the pair of extension portion of the side associated with the first functional unit that is configured to include a first extension width that is configured to increase starting from a first receiving edge to a first terminating end; and one of the extension member of the pair of extension portion of the side associated with the second functional unit is configured to include a second extension width that is configured to increase starting from a second receiving edge to a second terminating end.

The decrease in gap width and increase in extension width may be gradual. Alternatively, the decrease in gap width and increase in extension width may be stepwise.

According to an embodiment, the decrease in the first gap width and increase in width of the one of the extension member of the pair of extension portion of the side associated with the second functional unit are configured such that wider gap width at the first receiving edge is configured to displacably receive narrower extension width of the extension member, associated with the second functional unit, positioned at the second receiving edge. In a further combinable embodiment, the decrease of the first gap width and the increase of the extension member width, associated with the second functional unit, are configured such that movement of the extension member associated with the second functional unit along the first gap along the translation axis positions the first functional unit and the second functional unit in a non-displaceable position. In yet further combinable embodiment, the first gap width along the first guide channel and the extension member width, associated with the second functional unit, are configured such that in the non-displaceable position a) the first terminating end and the second receiving edge are proximal such as adjacent to each other, and b) the first receiving edge and the second terminating edge are proximal such as adjacent to each other. In yet further combinable embodiment, the decrease of the first gap width and the increase of the extension member width, associated with the second functional unit, are configured such that movement of the extension member associated with the second functional unit along the first gap along the translation axis orients the at least two electrical pins in alignment with the at least two electrical slots and/or to orient the at least two electrical slots in alignment with the at least two electrical pins such that each of the at least two electrical pins is received in the corresponding one of the at least two electrical slots. The at least two electrical pins and at least two electrical slots may be positioned respectively adjacent to one of a) the first terminating end and second receiving edge, or b) the first receiving edge and second terminating end or c) the second terminating end and first receiving edge, or d) second receiving edge and first terminating end. Thus, the change in gap width and extension member width may be gradual or step wise and thus, allows for preventing bending of the at least two electrical pins and/or at least two electrical slots during establishment of the electrical connection.

According to an embodiment, the decrease in the second gap width and increase in width of one of the extension member of the pair of extension portion of the side associated with the first functional unit are configured such that wider gap width g at the second receiving edge is configured to displacably receive narrower extension width W of the extension member, associated with the first functional unit, positioned at the first receiving edge. In a further combinable embodiment, the decrease of the second gap width and the increase of the extension member width, associated with the first functional unit, are configured such that movement of the extension member associated with the first functional unit along the second gap along the translation axis positions the second functional unit and the first functional unit in a non-displaceable position. In yet further combinable embodiment, the second gap width g along the second guide channel and the extension member width, associated with the first functional unit, are configured such that in the non-displaceable position a) the first terminating end and the second receiving edge are proximal such as adjacent to each other, and b) the first receiving edge and the second terminating edge are proximal such as adjacent to each other. In yet further combinable embodiment, the decrease of the second gap width and the increase of the extension member width, associated with the first functional unit, are configured such that movement of the extension member associated with the first functional unit along the second gap along the translation axis orients the at least two electrical pins in alignment with the at least two electrical slots and/or to orient the at least two electrical slots in alignment with the at least two electrical pins such that each of the at least two electrical pins is received in the corresponding one of the at least two electrical slots. The at least two electrical pins and at least two electrical slots may be positioned respectively adjacent to one of a) the first terminating end and second receiving edge, or b) the first receiving edge and second terminating end or c) the second terminating end and first receiving edge, or d) second receiving edge and first terminating end. Thus, the change in gap width g and extension member width W may be gradual or step wise and thus, allows for preventing bending of the at least two electrical pins and/or at least two electrical slots during establishment of the electrical connection.

The term displacably refers to possibility of movement of the extension member along the width of the gap in which the extension member is received. The displaceable receiving narrower portion of the extension member in the wider gap width of the guide channel ensures that precise alignment of the extension member and receiving guide channel is not required. This is particularly useful if the hearing device is being used by elderly, who generally have deteriorated motor skills or children having clumsy motor skills.

The term non-displaceable position refers to preventing movement of the extension member along the width of the gap in which the extension member is received.

According to an embodiment, the hearing aid further where one of the first surface or the second surface comprises a first engagement unit; and another of the first surface or the second surface comprises a second engagement unit, the first engagement unit and the second engagement unit configured to interact such that the first functional unit and the second functional unit are movably locked with each other.

The engagement of the first engagement unit and the second engagement unit indicates that the first functional unit and the second functional unit are in coupled state, thereby indicating that the locking mechanism using the actuator can be initiated.

In one embodiment, one of the first surface or the second surface comprises a first engagement unit comprising a notch; and another of the first surface or the second surface comprises a second engagement unit comprising a projection extending at least substantially perpendicular to the another of the first surface or the second surface. The projection is configured to resiliently snap lock into the notch to movably lock the first functional unit and the second functional unit with each other.

In another embodiment, one of the first surface or the second surface comprises a first engagement unit comprising a first magnet; and another of the first surface or the second surface comprises a second engagement unit comprising a second magnet. The first magnet and the second magnet include opposite poles and are aligned such that the first magnet and second magnet are attracted towards each other when the first functional unit and the second functional unit are in coupled position, i.e. are movably locked with each other. Using magnets allows for a mechanical free solution and thus a more wear resistant implementation. The first magnet and the second magnet may configured to be flush with respective surface to which the first magnet and are comprised in. This allows for a smooth movement of the first functional unit and second functional unit along the translation axis.

The term "movably lock" means that the first functional unit and the second functional unit are adapted to move relative to each other by overcoming the snap-locking resistance or magnet-attraction resistance, i.e. when a moveable force exceeding the snap-lock resistance or magnet-attraction resistance is applied, along the translation axis, to one of the functional units relative to the another functional unit. Thereafter, the first functional unit and the second functional unit may be decoupled by applying the detaching force. Typically, the snap-lock resistance or magnet-attraction resistance is higher than the specific magnitude of the detaching force that is required to decouple the two functional units.

In order to provide a higher resistance, the skilled person would appreciate that the earlier recited embodiments may be combined. The hearing aid may include a first engagement unit comprising a notch and a first magnet and a second engagement unit comprising a projection corresponding to the lock and a second magnet. In other embodiments, the properties of notch-projection and/or first magnet-second magnet may be altered in order to provide an increased or decreased resistance. Such variations are typically useful in accommodating skills, required for decoupling the functional units, of the user group of the hearing aid.

Having a hearing aid utilizing the disclosed notch-projection and/or first magnet-second magnet arrangement provides an additional feature for avoiding accidental decoupling of the first functional unit and the second functional unit even when the moveable element is not in the second position. Furthermore, including the notch and the projection and/or the first magnet and second magnet at respective functional unit surfaces, which are adapted to abut surficially allow for an arrangement that is invisible when the first functional unit and the second functional units are coupled, thereby providing an aesthetically appealing hearing aid.

According to an embodiment, the hearing aid further includes at least two electrical pins and at least two electrical slots being configured to receive corresponding of the at least two electrical pins for providing electrical connection between the first functional unit and the second functional unit. The at least two electrical pins and at least two electrical slots are positioned respectively adjacent to one of a) the first terminating end and second receiving edge, or b) the first receiving edge and second terminating end, or c) the second terminating end and first receiving edge, or d) second receiving edge and first terminating end. The hearing aid further includes an alignment structure comprising at least one elongated paths provided around the at least two electrical pins and/or at least two electrical slots. The at least one elongated path is configured to orient the at least two electrical pins in alignment with the at least two electrical slots and/or to orient the at least two electrical slots in alignment with the at least two electrical pins such that each of the at least two electrical pins is received in the corresponding one of the at least two electrical slots. Thus, the alignment structure is configured to prevent bending of the at least two electrical pins and/or at least two electrical slots during establishment of the electrical connection.

In an embodiment, when electrical connection between the first functional unit and the second functional unit, the first functional unit and second functional unit are in coupled state.

The at least one elongated path may include a gradual or stepwise reduction of a receiving width/diameter of the at least one elongated path as a function of a distance from a receiving section of the at least one elongated path. The receiving section may be defined as an opening that allows insertion of one of the at least two electrical pin or one of the at least two electrical slot into the one of the at least one elongated paths.

It is to be understood that contact between the at least two electrical pin and the at least two electrical slot establishes electrical connection between the first functional unit and the second functional unit.

In different embodiments, the at least one elongated paths comprises a first section of a first length along the translation axis and a second section of a second length along the translation axis, a combination of the first length and the second length defining length of the each of the at least one elongated path. In one embodiment, at least one of the at least two electrical pins is positioned within the elongated path such that the at least one of the at least two electrical pins only runs along the first section and the second section extends between the receiving section and a tip of the at least one of the at least two electrical pins. In another embodiment, at least one the at least two electrical slots is positioned within the elongated path such that the one of the at least two electrical slots only runs along the first section and the second section extends between the receiving section and a tip of the at least two electrical slot.

In an embodiment, the elongated paths are only provided around the at least two electrical pins. In another embodiment, the elongated paths are only provided around the at least two electrical slots. These two preceding embodiments may be useful because providing the elongated paths only either around the pins or around the slots allow for easier manufacturing process. In yet another embodiment, the one elongated path is provided around one of the at least two electrical pins but not around the corresponding slot and another elongated path is provided around one of the at least two electrical slots but not around the corresponding electrical pin. This implementation may further be provided with an alternate arrangement of the elongated paths between electrical pin surrounded by the elongate path followed by neighboring electrical slot being surrounded by the elongated path. This implementation may however, be also useful because providing the elongated path surrounding alternately between electrical pins and neighboring electrical slots may allow for a more reliable orientation during establishing electrical connection.

According to an embodiment, the hearing aid further includes at least two electrical pins and at least two electrical slots, the at least two electrical pins and at least two electrical slots being positioned respectively adjacent to one of a) the first terminating end and second receiving edge, or b) the first receiving edge and second terminating end, or c) the second terminating end and first receiving edge, or d) second receiving edge and first terminating end. The hearing aid further includes at least one of a pin region or a slot region comprising at least one capillary stop. The region is defined by a space provided between the at least two electrical pins and the slot region is defined by a space provided between the at least two electrical slots.

The at least two electrical pins and the at least two electrical slots may be arranged in a corresponding patterns. The term corresponding pattern includes a pin pattern comprising position of each pin of the at least two electrical pins at one of the first terminating end or the second terminating end and slot pattern comprising position of each slot of the at least two electrical slots at another of the first terminating end or the second terminating end such that when the first functional unit and the second functional unit are moved along the translation axis for coupling, then each pin is brought closer and in line to a matching slot. The matching relates to establishing electrical connection between the first functional unit and the second functional unit.

In an embodiment, the capillary stop includes at least one capillary channel configured to transfer liquid away from the at least two electrical pins and/or at least two electrical slots using capillary attraction i.e. transferring liquid in channels driven through capillary force. The capillary channels are typically narrow channels and the skilled person would realise the width of these channels in accordance with the desired capillary stop requirement in relation to space constraints.

Electrical components such as electrical pins and electrical slots or components within the functional units are sensitive to damage from liquids. With liquid, harming particles (e.g. ions) may access sensitive areas inside the electrical parts of and may cause for example, corrosion, electrochemical migration and/or short circuiting the electronic device. Thus, the capillary stop is configured to restrict ingress of liquid. This allows for preventing damage of electrical components.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects.

These and other aspects, features and/or technical effect will be apparent from and elucidated with reference to the illustrations described hereinafter in which:

FIG. 1A illustrates a battery chamber, FIG. 1B illustrates a chamber cover, FIG. 1C illustrates battery chamber and the chamber cover in unlocked position and FIG. 1D illustrates battery chamber and chamber cover in locked position;

FIG. 2 illustrates a hearing aid comprising a first functional unit and a second functional unit according to an embodiment of the disclosure;

FIG. 3C illustrates cross section view of dashed section of FIG. 3A as seen in direction X according to an embodiment of the disclosure, FIG. 3D illustrates cross section view of dashed section of FIG. 3B as seen in direction X according to an embodiment of the disclosure.

FIG. 9A illustrates a first guide channel and a second guide channel according to an embodiment of the disclosure and FIG. 9B illustrates a first extension portion and the second extension portion moving along a translation axis according to an embodiment of the disclosure.

DETAILED DESCRIPTION

Figure 1:
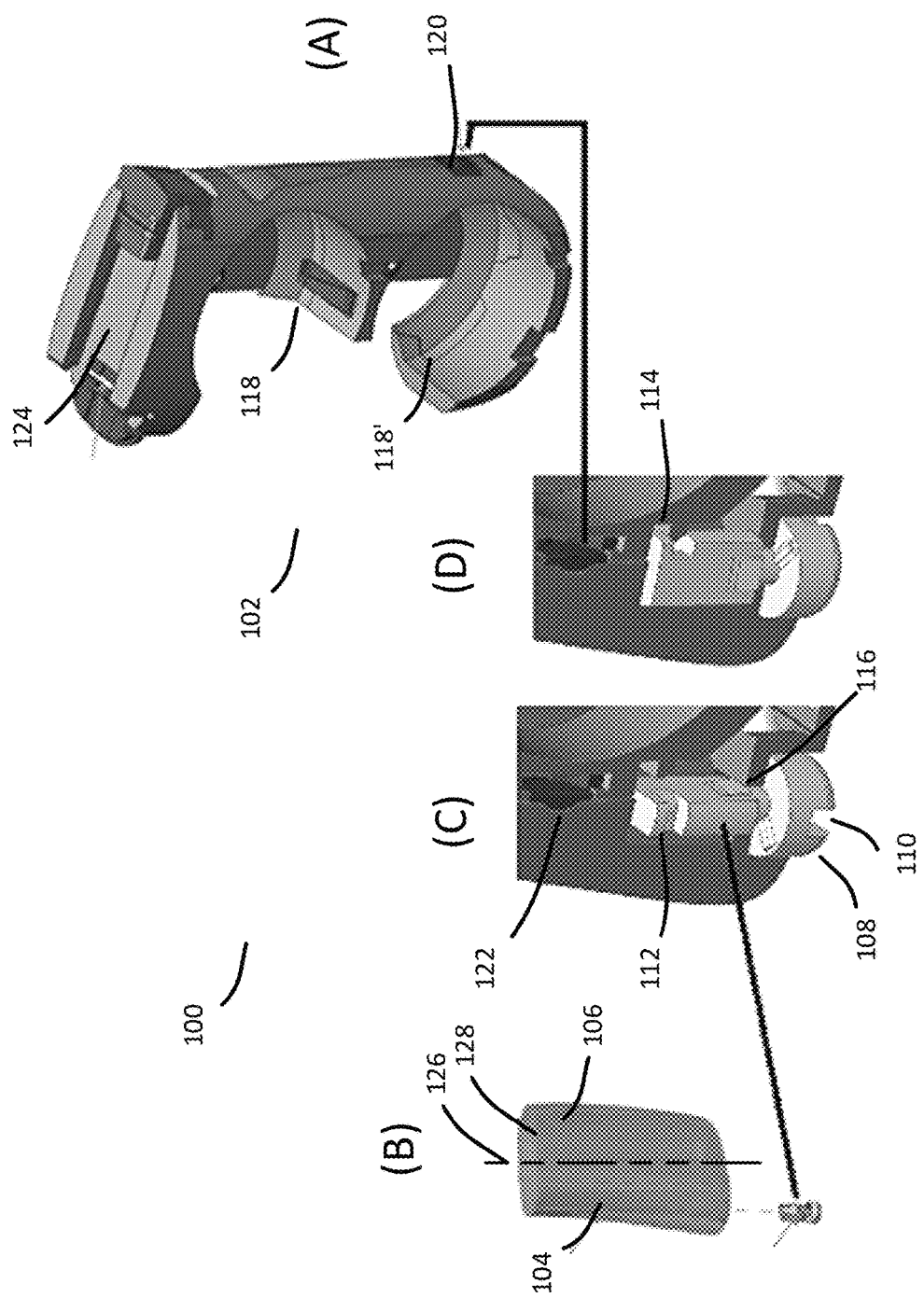
FIG. 1 illustrates different components of a battery compartment forming a second functional unit according to an embodiment of the disclosure, where

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus and methods are described by various blocks, functional units, modules, components, etc.

In the description below, same reference numeral generally illustrate the same component of the hearing aid device.

Now referring to FIG. 1 that illustrates different components of a battery compartment forming a second functional unit according to an embodiment of the disclosure. In particular FIG. 1A illustrates a battery chamber, FIG. 1B illustrates a chamber cover, FIG. 1C illustrates battery chamber and the chamber cover in unlocked position and FIG. 1D illustrates battery chamber and chamber cover in locked position.

According to an embodiment, the hearing aid includes a battery compartment 100 (shown in disassembled form) comprising a battery chamber 102 and a chamber cover 104. The battery chamber is configured to hold the battery (not shown, in receptacles 118 and/or 118') and is adapted to slide into the battery chamber along a guide rail 106 in an axial direction 126. The battery chamber includes a cut out section 114 provided at an external surface of the battery chamber. The cut out section is adapted to receive a corresponding cut out element 112 of a rotatable screw 108 for locking the battery chamber 102 with the chamber cover 104.

Additionally or alternatively, one of the guide chamber and chamber cover includes a hole such as a hole 122 provided at inner surface of the chamber cover whereas another of the guide chamber and chamber cover includes a projected piece such as a projected piece 120 provided at an outer surface of the battery chamber that snap locks in to the hole when the battery chamber is completely received in the chamber cover.

In an embodiment, the chamber cover may include a through-going hole 116 that is adapted to allow insertion of the rotatable screw 108 such that the rotatable screw is accessible (such as at a slot 110) for rotation from outside of the battery cover whereas the cut out element is rotatable within the battery cover when a rotational force on the rotatable screw is applied.

The chamber cover may include a one piece assembly with a single opening 128 from where the battery chamber 102 is inserted in the axial direction 104 within the chamber cover 104.

One section of the battery cover may be adapted to close the opening 128 of the chamber cover when the chamber cover is completely inserted in the chamber cover. An outer surface 124 of the section may define the second surface of the second functional unit.

FIG. 2 illustrates a hearing aid comprising a first functional unit and a second functional unit according to an embodiment of the disclosure. The hearing aid includes a first functional unit 202 and a second functional unit 102. The second functional unit 102 is configured to removably couple with the first functional unit 202. The coupling is configured to provide at least a mechanical connection between the first functional unit and the second functional unit. Such coupling may be provided by moving, in the direction 204, the first functional unit and the second functional unit along a translation axis 206. In the illustrated figure, 208 represents the actuator and 210 illustrates a U-shaped notch adapted to receive the end of a corresponding U-shaped tool adapted to rotate the actuator.

Figure 3B:
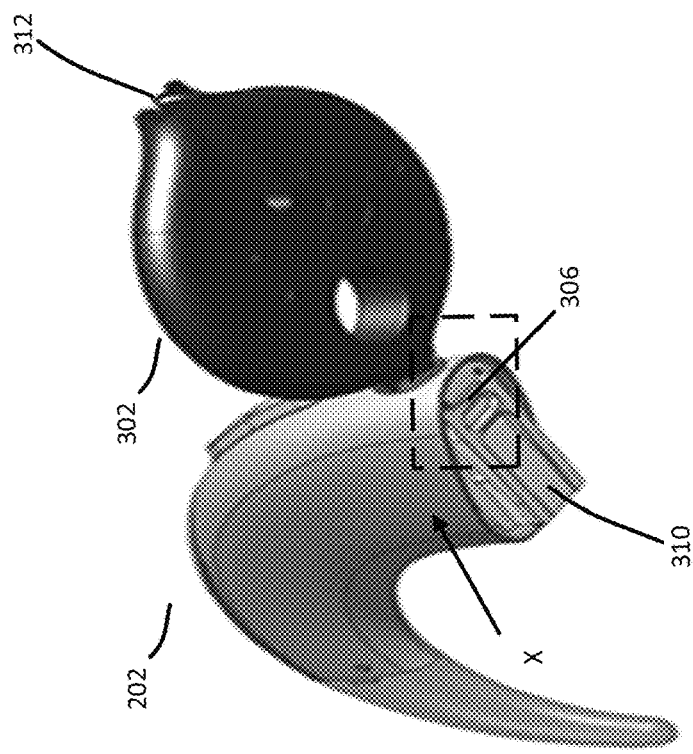
FIG. 3B illustrates a locking mechanism with a part of the moveable unit protruding out of the first functional unit according to an embodiment of the disclosure.
Figure 3A:
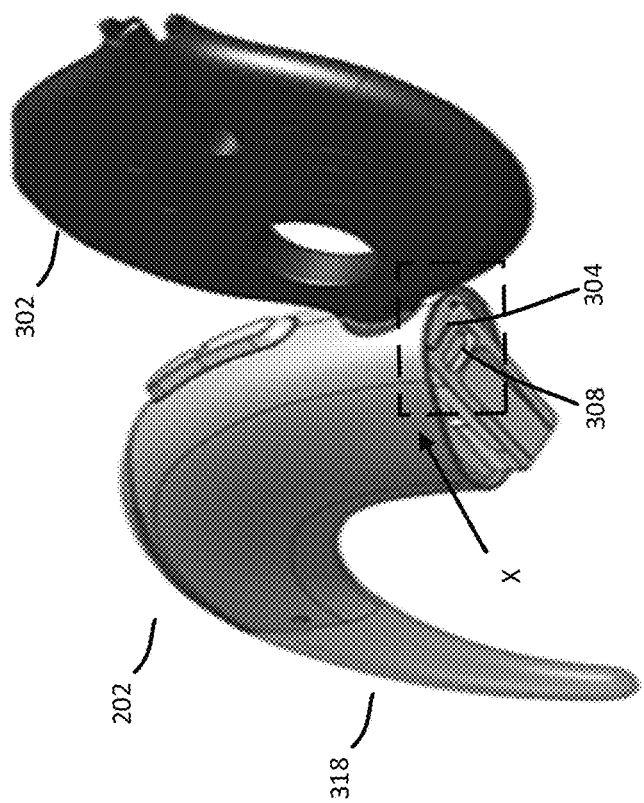
FIG. 3A illustrates a locking mechanism with the moveable unit contained entirely with in the first functional unit according to an embodiment of the disclosure.

FIG. 3A illustrates a locking mechanism with the moveable unit contained entirely with in the first functional unit according to an embodiment of the disclosure. FIG. 3B illustrates a locking mechanism with a part of the moveable unit protruding out of the first functional unit according to an embodiment of the disclosure. FIG. 3C illustrates cross section view of dashed section of FIG. 3A as seen in direction X according to an embodiment of the disclosure and FIG. 3D illustrates cross section view of dashed section of FIG. 3B as seen in direction X according to an embodiment of the disclosure.

The first functional unit 202 comprises a moveable element 314 that is configured to move between a first position (see FIGS. 3A and 3C) and a second position (see FIG. 3B and FIG. 3D) such that in the first position, the moveable element 314 is contained entirely within the first functional unit 202 and in the second position, a part 306 of the moveable element is configured to protrude out of the first functional unit 202 such as through the slit 304. The second functional unit 102 includes a recess 316 configured to receive the part 306 of the moveable element that protrudes out of the first functional unit 202 such that the first functional unit and the second functional unit are immovably locked with respect to each other in response to the moveable element being received in the recess along the translational axis (206, FIG. 2).

Figure 3E:
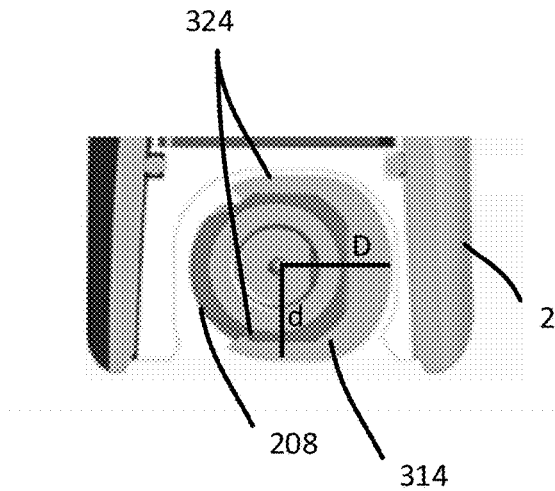
FIG. 3E illustrates the first position as seen from direction Y (FIG. 2) according to an embodiment of the disclosure and FIG. 3F illustrates the second position as seen from direction Y (FIG. 2) according to an embodiment of the disclosure.

FIG. 3E illustrates the first position as seen from direction Y (FIG. 2) according to an embodiment of the disclosure and FIG. 3E illustrates the second position as seen from direction Y (FIG. 2) according to an embodiment of the disclosure. For simplicity reasons, only the first functional unit is shown and therefore the second position is not completely illustrated in FIG. 3F. As shown in FIG. 3E, the moveable element 314 is contained entirely within the first functional unit 202 when in the first position and in the second position as illustrated in FIG. 3F, a part 306 of the moveable element 314 protrudes out of the first functional element 202.

In FIGS. 3A and 3B, 308 illustrates the first engagement unit in form of a notch, 310 illustrates the first surface and 302 illustrates a actuator tool that is configured to rotate the actuator. The skilled person would appreciate that in an embodiment where the actuator comprises the antenna cable output port, the pass-through passage as defined by the hole section 312 all the way to the actuator (208, see FIG. 2) allows for using the actuator even when the antenna cable is in connection with the antenna cable outputport. 318 illustrates an ear hook that is adapted to allow resting of the hearing aid on the user's ear and for positioning the hearing aid as a behind-the-ear device. Also, 326 illustrates the rotation axis.

According to an embodiment, as illustrated in FIG. 3, the moveable element 314 comprises a rotatable unit 314 configured to rotate around a rotation axis (326, FIG. 3C). The actuator 208 includes a rotatable actuator 208 configured to rotate around the rotation axis (326, FIG. 3C), the rotation of the actuator is configured to rotate the rotatable unit 314 around the rotation axis between the first position (see FIG. 3E) and second position (see FIG. 3F).

Figure 3F:
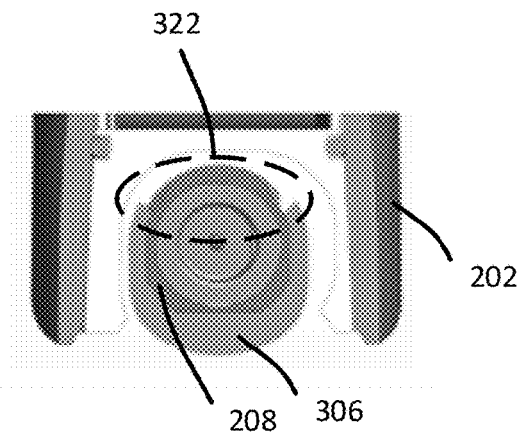

According to an embodiment, referring to FIG. 3E and FIG. 3F, the rotatable unit 314 comprises a primary section 306 defining the part that is adapted to protrude out of the first functional unit and a secondary section 324. A primary distance D defining a distance between the rotation axis 326 and an outer periphery of the primary section 306 is more than a second distance d defining a distance between the rotation axis 326 and an outer periphery of the secondary section 324. Usually, D represents the maximum distance between the rotation axis 326 and the outermost periphery of the primary section 306.

According to an embodiment, referring again to FIG. 3E and FIG. 3F, the rotatable unit 314 includes the primary section 306, the secondary section 324 and a peripheral gap 322 (as illustrated by the gap between 324). The peripheral gap being provided between the primary section and the secondary section or between a first part and a second part of a dual-part secondary section (such dual part secondary section is illustrated in the FIGS. 3E and 3F).

In an embodiment, the moveable element 314 is coupled to the actuator 208 (as shown by a dashed circle section in FIG. 3D). The actuator is at least partly comprised in the first functional unit 202 and accessible from outside a body of the first functional unit 202 (as shown in FIG. 2 and FIG. 3C). The actuator is configured to move the moveable element between the first position and the second position (as shown in FIG. 3).

In an embodiment, the first functional part 202 comprises a slit 304 configured to allow the part 306 of the moveable element 314 to protrude out of the first functional unit 202 in response to an actuation force applied to the actuator 208.

Figure 4:
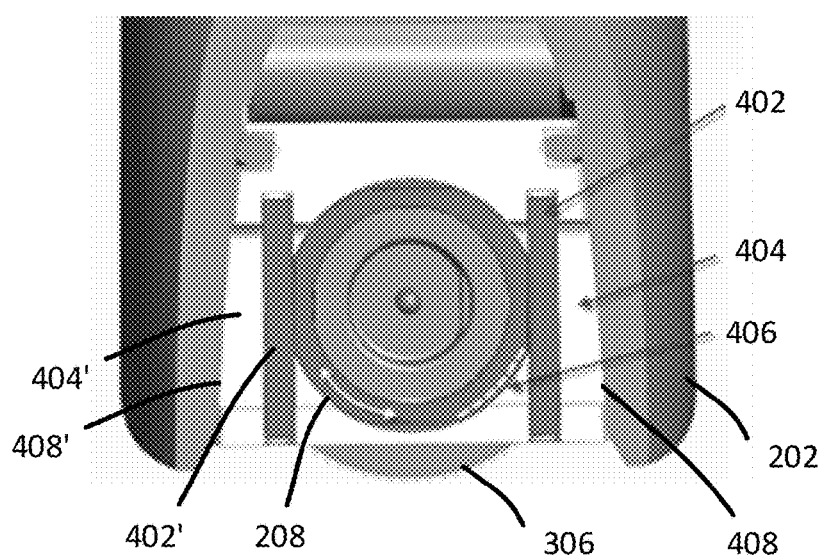
FIG. 4 illustrates a friction element according to an embodiment of the disclosure.

FIG. 4 illustrates a friction element according to an embodiment of the disclosure. The friction element (402, 402') is arranged within the first functional unit 202, the friction element (402, 402') is configured to cooperate with the moveable element 314 and/or actuator 208 such that the moveable element 314 moves between the first position and the second position in response to the actuation force that is above a friction threshold, which is defined by the friction between the friction element and moveable element and/or actuator 208. In the figure, 406 represents the part of the actuator 208 that is configured to apply the compression force to the friction element (402, 402') when the actuator is rotated around the rotation axis.

In an embodiment, the friction element (402, 402') is positioned within the first functional unit 202 such that a clearance (404, 404') is provided between the friction element (402, 402') and adjacent component such as inner wall (408, 408') of the first functional unit 202. The clearance (404, 404') is configured to accommodate the flex induced in the friction element (402, 402') because of the compression force applied by the moveable element and/or actuator 208.

In the illustrated embodiment, the friction element (402, 402') comprises at least one pair of friction sub-elements (402, 402') that are positioned on opposite end of the periphery of the actuator 208.

According to an embodiment, in the first position, the peripheral gap 322 is configured to face the slit 304. Alternatively, the outer periphery of the primary section 306 is configured to remain within the first functional unit 202 and the outer periphery of the secondary section 324 is configured to face the slit 304 while remaining within the first functional unit 202 with or without at least a section of the outer periphery of the secondary section 324 being flush with the slit 304. This embodiment is illustrated in FIG. 3E a section of the outer periphery of the secondary section 324 is flush with the slit 304.

According to an embodiment, in the second position, the outer periphery of the primary section 306 is configured to protrude out of the slit 304 and the outer periphery of the secondary section 324 and/or peripheral gap 322 is configured to remain within the first functional unit, as illustrated in FIG. 3F.

The hearing aid according to any of the preceding claims, wherein the first functional unit comprises a stop member configured to functionally couple to the actuator and/or rotatable unit for limiting rotation of the actuator and/or rotatable unit at at least one of the first position and the second position.

Figure 5:
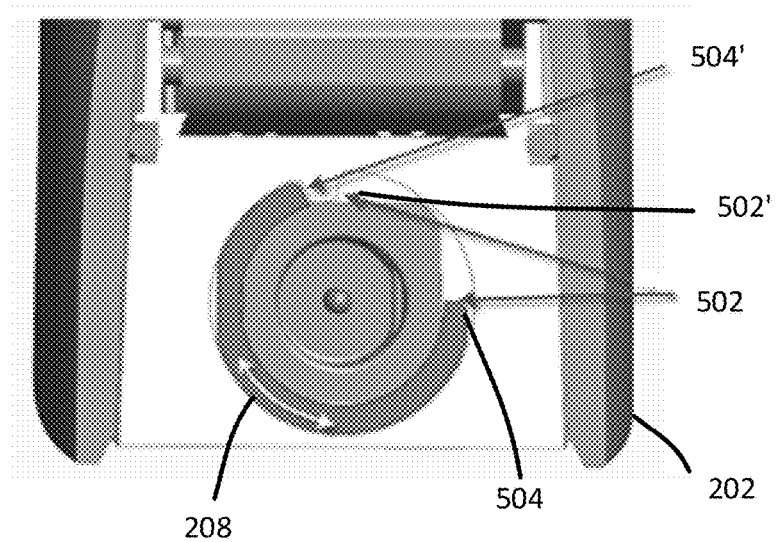
FIG. 5 illustrates a stop member according to an embodiment of the disclosure.

FIG. 5 illustrates a stop member according to an embodiment of the disclosure. The first functional unit 202 includes a stop member (502, 502') configured to functionally couple to the actuator 208 and/or rotatable unit for limiting rotation of the actuator 208 and/or rotatable unit at at least one of the first position and the second position. In an embodiment, this is implemented by interaction between the stop member (502, 502') and at least one extended projection (504, 504') of the actuator 208 wherein the extended projection includes a peripheral extension or cut out section defining the extension (504, 504') at surface of the actuator, the extension being configured to interact with the stop member at least at the first position or the second position. Interaction between extension 504 and 502 as shown in the Figure define the first position and interaction between extension 504' and 502' (when the actuator is rotated) define the second position.

According to an embodiment, and referring to FIG. 1 and FIG. 3, the first functional unit 202 comprises a first surface 310 comprising the slit 304 and the second functional unit 102 comprises a second surface 124 comprising the recess 316, wherein the first surface 310 and the second surface 124 are configured to abut surfacially when the first functional unit 202 and the second functional unit 102 are arranged immovably with respect to each other.

According to an embodiment, the slit 304 of the first functional unit 202 is configured to align with the recess 316 of the second functional unit 102 when the first functional unit 202 and the second functional unit 102 are positioned in the immovably locked position.

Figures 6A, 6B:
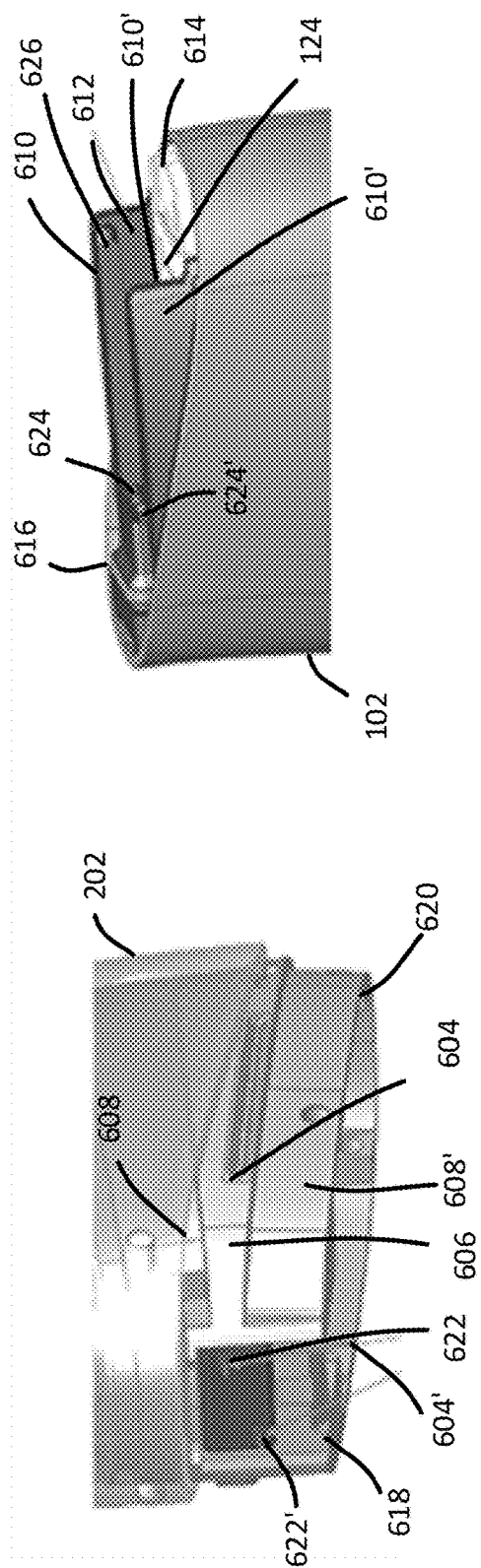
FIG. 6A illustrates a first guide channel according to an embodiment of the disclosure and FIG. 6B illustrates a second guide channel according to an embodiment of the disclosure.

FIG. 6A illustrates a first guide channel according to an embodiment of the disclosure and FIG. 6B illustrates a second guide channel according to an embodiment of the disclosure.

According to an embodiment, the first functional unit 202 includes a first pair of at least substantially parallel sides (604, 604'), each comprising a first guide channel 606 defined by a first gap between a pair of extension portions (608, 608') of the side. Further, the second functional unit 102 comprises a second pair of at least substantially parallel sides (610, 610'), each comprising a second guide channel (612) defined by a second gap between the second surface 124 and a second extension portion 626 of the side. One of the pair of extension portions (608, 608') is adapted to slide between a second receiving edge 614 of the second surface 124 though the second guide channel 612 to a second terminating end 616 of the second surface 124. The second extension portion 626 is adapted to slide between a first receiving edge 618 of the first surface though the first guide channel 606 to a first terminating end 620 of the first surface.

According to an embodiment, one of the first surface 310 or the second surface 124 includes a first engagement unit; and another of the first surface 310 or the second surface 124 includes a second engagement unit, the first engagement unit and the second engagement unit configured to interact such that the first functional unit and the second functional unit are movably locked with each other. For example. referring to FIGS. 1 and 3, the second engagement unit may include a projected piece provided on the second surface 124 and the first surface may include a notch 308 that is adapted to receive the projected piece in a snap lock fashion.

According to an embodiment, referring again to FIG. 6, the hearing aid includes at least two electrical pins (622, 622') and at least two electrical slots (624, 624') being configured to receive corresponding of the at least two electrical pins (622, 622') for providing electrical connection between the first functional unit 202 and the second functional unit 102. The at least two electrical pins and at least two electrical slots are positioned respectively adjacent to one of a) the first terminating end 620 and second receiving edge 614, orb) the first receiving edge 618 and second terminating end 616 (as illustrated in FIG. 6A and FIG. 6B), or c) the second terminating end 616 and first receiving edge 618, or d) second receiving edge 614 and first terminating end 620. In a combination embodiment, as illustrated in FIG. 7, the hearing aid further includes an alignment structure (702, 702', 708, 710, 710', 712) including at least one elongated path provided around the at least two electrical pins (622, 622') and/or at least two electrical slots (624, 624'), wherein the at least one elongated path is configured to orient the at least two electrical pins (622, 622') in alignment with the at least two electrical slots (624, 624') such that each of the at least two electrical pins (622, 622') is received in the corresponding one of the at least two electrical slots (624, 624').

According to an embodiment, as illustrated in FIG. 7, the at least two electrical pins (622, 622') are connected to a pin block 704 that may be comprised in one of the first functional unit or the second functional unit. The at least two electrical slots (624, 624') are connected to a slot block 706 that may be comprised in another of the first functional unit or the second functional unit. 726 represent the receiving section of the alignment structure.

Figure 7A:
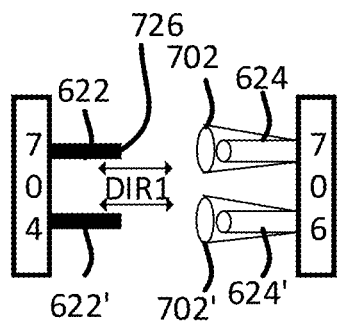
FIG. 7A illustrates an alignment structure around individual electrical pin according to an embodiment.

FIG. 7A illustrates an alignment structure around individual electrical pin according to an embodiment. The alignment structure (702, 702') is individually surrounding the electrical slots 624 and 624' respectively. During connection step, the at least two pins (622, 622') and at least two slots (624, 624') are moved relative to each other in the direction DIR1. The narrowing of the alignment structure allows orientation of the at least two pins in such a way that they are received in the at least two slots without the two pins getting bent.

Figure 7B:
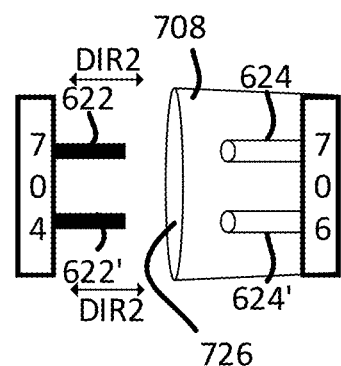
FIG. 7B illustrates an alignment structure around the electrical pin according to an embodiment.

FIG. 7B illustrates an alignment structure around the electrical pin according to an embodiment. The alignment structure 708 surrounds the slot block 706 comprising the electrics slots 624, 624'. During connection step, the pin block 704 comprising the electrical pins (622, 622') and slot block 706 comprising the electrical slots (624, 624') are moved relative to each other in the direction DIR2. The narrowing of the alignment structure 708 allows orientation of the at least two pins in such a way that they are received in the at least two slots without the two pins getting bent.

Figure 7C:
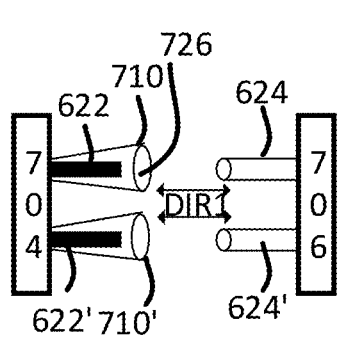
FIG. 7C illustrates an alignment structure around individual electrical slot according to an embodiment.

FIG. 7C illustrates an alignment structure around individual electrical slot according to an embodiment. The alignment structure (710, 710') is individually surrounding the electrical pins 622 and 622' respectively. During connection step, the at least two pins (622, 622') and at least two slots (624, 624') are moved relative to each other in the direction DIR1. The narrowing of the alignment structure allows orientation of the at least two slots in such a way that at least two pins are received in the at least two slots without the at least two pins getting bent.

Figure 7D:
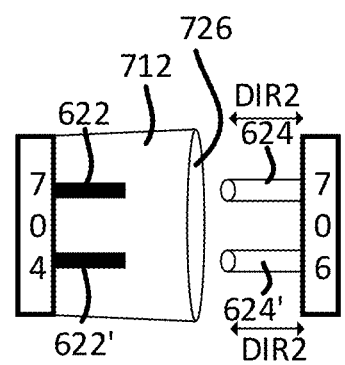
FIG. 7D illustrates an alignment structure around the electrical slot according to an embodiment.

FIG. 7D illustrates an alignment structure around the electrical slot according to an embodiment. The alignment structure 712 surrounds the pin block 704 comprising the electrics pins (622, 622'). During connection step, the pin block 704 comprising the electrical pins (622, 622') and slot block 706 comprising the electrical slots (624, 624') are moved relative to each other in the direction DIR2. The narrowing of the alignment structure 712 allows orientation of the at least two slots in such a way that the at least two pins are received in the at least two slots without the two pins getting bent.

Figure 8:
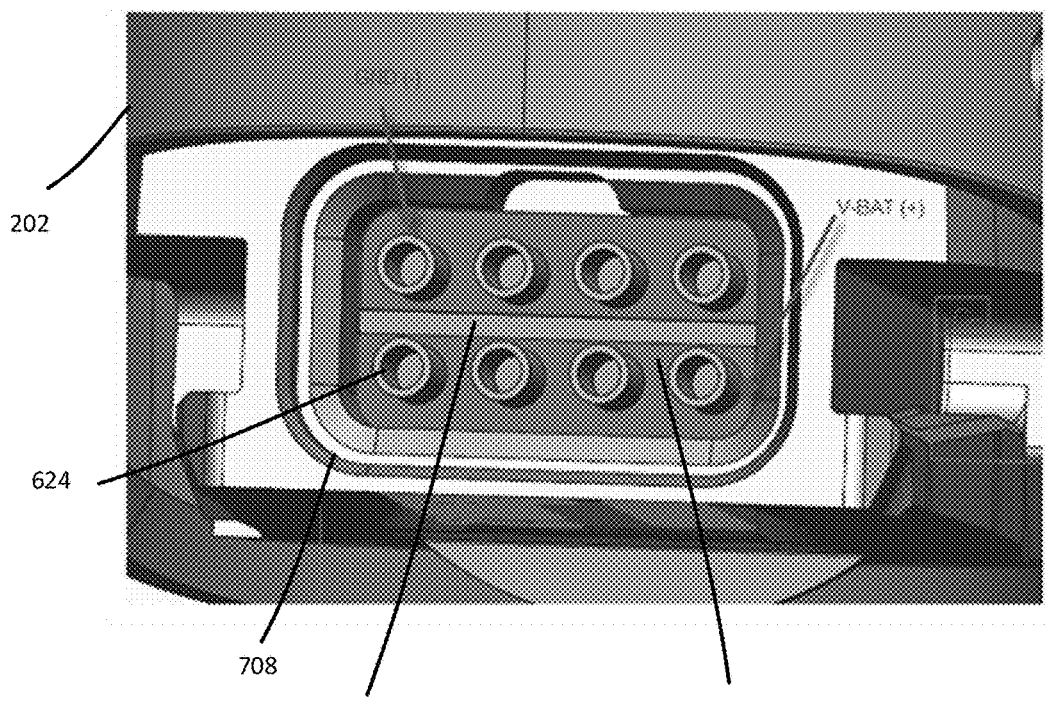
FIG. 8 illustrates a capillary stop according to an embodiment of the disclosure.

FIG. 8 illustrates a capillary stop according to an embodiment of the disclosure. In the illustrative embodiment, the at least two electrical slots 624 are positioned adjacent to the first receiving edge of the first functional unit 202. The slot region 804, defined by the space between the at least two electrical slots is provided with a capillary stop 802. It is apparent that such one or more capillary stops may be provided at the slot region and/or pin region. The figure further illustrates the alignment structure 708.

FIG. 9A illustrates a first guide channel and a second guide channel according to an embodiment of the disclosure and FIG. 9B illustrates a first extension portion and the second extension portion moving along a translation axis according to an embodiment of the disclosure.

According to an embodiment, the hearing aid includes the first gap that is configured to decrease in a first gap width (from G to G') starting from a first receiving edge 618 to a first terminating end 620; and the second gap is configured to decrease in a second gap width (from g to g') starting from a second receiving edge 614 to a second terminating end 616. The hearing aid further includes one of the extension member 608' of the pair of extension portion of the side associated with the first functional unit 202 that is configured to include a first extension width that is configured to increase (from W to W') starting from a first receiving edge 618 to a first terminating end 620; and one of the extension member 626 of the pair of extension portion of the side associated with the second functional unit 102 is configured to include a second extension width that is configured to increase (from w to w') starting from a second receiving edge 614 to a second terminating end 616.

The decrease in gap width and increase in extension width may be gradual, as shown in the illustrated figures. Alternatively, the decrease in gap width and increase in extension width may be stepwise.

According to an embodiment, the decrease in the first gap width (from G to G') and increase in width (from w to w') of the one of the extension member 626 of the pair of extension portion of the side associated with the second functional unit 102 are configured such that wider gap width G at the first receiving edge 618 is configured to displacably receive narrower extension width w of the extension member 626, associated with the second functional unit 102, positioned at the second receiving edge 614. In a further combinable embodiment, the decrease of the first gap width (from G to G') and the increase of the extension member width (from w to w'), associated with the second functional unit 102, are configured such that movement of the extension member 626 associated with the second functional unit 102 along the first gap along the translation axis (Y, see FIG. 2) positions the first functional unit 202 and the second functional unit 102 in a non-displaceable position. In yet further combinable embodiment, the first gap width G along the first guide channel 606 and the extension member width w, associated with the second functional unit 102, are configured such that in the non-displaceable position a) the first terminating end 620 and the second receiving edge 614 are proximal such as adjacent to each other, and b) the first receiving edge 618 and the second terminating edge 616 are proximal such as adjacent to each other. In yet further combinable embodiment, the decrease of the first gap width (from G to G') and the increase of the extension member width (from w to w'), associated with the second functional unit 102, are configured such that movement of the extension member 626 associated with the second functional unit 102 along the first gap along the translation axis (Y, see FIG. 2) orients the at least two electrical pins in alignment with the at least two electrical slots and/or to orient the at least two electrical slots in alignment with the at least two electrical pins such that each of the at least two electrical pins is received in the corresponding one of the at least two electrical slots. The at least two electrical pins and at least two electrical slots may be positioned respectively adjacent to one of a) the first terminating end 620 and second receiving edge 614, or b) the first receiving edge 618 and second terminating end 616 or c) the second terminating end 616 and first receiving edge 618, or d) second receiving edge 614 and first terminating end 620. Thus, the change in gap width (from G to G') and extension member width (from w to w') may be gradual or step wise and thus, allows for preventing bending of the at least two electrical pins and/or at least two electrical slots during establishment of the electrical connection.

According to an embodiment, the decrease in the second gap width (from g to g') and increase in width (from W to W') of one of the extension member 608' of the pair of extension portion of the side associated with the first functional unit 202 are configured such that wider gap width g at the second receiving edge 614 is configured to displacably receive narrower extension width W of the extension member 608', associated with the first functional unit 202, positioned at the first receiving edge 618. In a further combinable embodiment, the decrease of the second gap width (from g to g') and the increase of the extension member width (w to w'), associated with the first functional unit 202, are configured such that movement of the extension member 608' associated with the first functional unit 202 along the second gap along the translation axis (Y, see FIG. 2) positions the second functional unit 102 and the first functional unit 202 in a non-displaceable position. In yet further combinable embodiment, the second gap width g along the second guide channel and the extension member width W, associated with the first functional unit 202, are configured such that in the non-displaceable position a) the first terminating end 620 and the second receiving edge 614 are proximal such as adjacent to each other, and b) the first receiving edge 618 and the second terminating edge 616 are proximal such as adjacent to each other. In yet further combinable embodiment, the decrease of the second gap width (from g to g') and the increase of the extension member width (from W to W'), associated with the first functional unit 202, are configured such that movement of the extension member 608' associated with the first functional unit 202 along the second gap along the translation axis (Y, see FIG. 2) orients the at least two electrical pins in alignment with the at least two electrical slots and/or to orient the at least two electrical slots in alignment with the at least two electrical pins such that each of the at least two electrical pins is received in the corresponding one of the at least two electrical slots. The at least two electrical pins and at least two electrical slots may be positioned respectively adjacent to one of a) the first terminating end 620 and second receiving edge 614, or b) the first receiving edge 618 and second terminating end 616 or c) the second terminating end 616 and first receiving edge 618, or d) second receiving edge 614 and first terminating end 620. Thus, the change in gap width g and extension member width W may be gradual or step wise and thus, allows for preventing bending of the at least two electrical pins and/or at least two electrical slots during establishment of the electrical connection.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A hearing aid comprising
a first functional unit;
a second functional unit configured to removably couple with the first functional unit, the coupling being configured to provide at least a mechanical connection between the first functional unit and the second functional unit; wherein
the first functional unit comprises a moveable element that is configured to move between a first position and a second position such that in the first position, the moveable element is contained entirely within the first functional unit and in the second position, a part of the moveable element is configured to protrude out of the first functional unit, the second functional unit comprises a recess configured to receive the part of the moveable element that protrudes out of the first functional unit such that the first functional unit and the second functional unit are immovably locked with respect to each other in response to the moveable element is received in the recess, wherein the moveable element is coupled to an actuator, at least partly comprised in the first functional unit and accessible from outside a body of the first functional unit, the actuator being configured to move the moveable element between the first position and the second position, wherein the first functional unit comprises a slit configured to allow the part of the moveable element to protrude out of the first functional unit in response to an actuation force applied to the actuator.

2. The hearing aid according to claim 1, further comprising a friction element arranged within the first functional unit, the friction element being configured to cooperate with the moveable element and/or actuator such that the moveable element moves between the first position and the second position in response to the actuation force that is above a friction threshold, which is defined by the friction between the friction element and moveable element and/or actuator.

3. The hearing aid according to claim 1, wherein
the moveable element comprises a rotatable unit configured to rotate around a rotation axis; and
the actuator comprises a rotatable actuator configured to rotate around the rotation axis, the rotation of the actuator is configured to rotate the rotatable unit around the rotation axis between the first position and second position.

4. The hearing aid according to claim 1, wherein
the rotatable unit comprises a primary section defining the part that is adapted to protrude out of the first functional unit and a secondary section; and
a primary distance defining a distance between the rotation axis and an outer periphery of the primary section is more than a second distance defining a distance between the rotation axis and an outer periphery of the secondary section.

5. The hearing aid according to claim 1, wherein the first functional unit comprises a stop member configured to functionally couple to the actuator and/or rotatable unit for limiting rotation of the actuator and/or rotatable unit at least one of the first position and the second position.

6. The hearing aid according to claim 1, wherein
the moveable element comprises a slidable unit configured to slide along a slide axis, the slidable unit comprising a first end and a second end;
the actuator comprises a slidable actuator configured to slide along the slide axis, the sliding of the actuator is configured to slide the slidable unit along the slide axis between the first position and second position;
in the first position, a first edge of the first end is configured to face the slit while remaining within the first functional unit with or without being flush with the slit; and
in the second position, the first edge of the first end is configured to protrude out of the slit and a second edge of the second end is configured to remain within the first functional unit.

7. The hearing aid according to claim 1, wherein the first functional unit comprises a first surface comprising the slit and the second functional unit comprises a second surface comprising the recess, wherein the first surface and the second surface are configured to abut surfacially when the first functional unit and the second functional unit are arranged immovably with respect to each other.

8. The hearing aid according to claim 7, wherein
one of the first surface or the second surface comprises a first engagement unit; and
another of the first surface or the second surface comprises a second engagement unit, the first engagement unit and the second engagement unit configured to interact such that the first functional unit and the second functional unit are movably locked with each other.

9. A hearing aid comprising
a first functional unit;
a second functional unit configured to removably couple with the first functional unit, the coupling being configured to provide at least a mechanical connection between the first functional unit and the second functional unit; wherein
the first functional unit comprises a moveable element that is configured to move between a first position and a second position such that in the first position, the moveable element is contained entirely within the first functional unit and in the second position, a part of the moveable element is configured to protrude out of the first functional unit,
the second functional unit comprises a recess configured to receive the part of the moveable element that protrudes out of the first functional unit such that the first functional unit and the second functional unit are immovably locked with respect to each other in response to the moveable element is received in the recess, wherein
the rotatable unit comprises a primary section defining the part that is adapted to protrude out of the first functional unit and a secondary section; and
a primary distance defining a distance between the rotation axis and an outer periphery of the primary section is more than a second distance defining a distance between the rotation axis and an outer periphery of the secondary section,
wherein the rotatable unit comprises the primary section, the secondary section and a peripheral gap, the peripheral gap being provided between the primary section and the secondary section or between a first part and a second part of a dual-part secondary section.

10. The hearing aid according to claim 9, wherein
in the first position, the peripheral gap is configured to face the slit or the outer periphery of the primary section is configured to remain within the first functional unit and the outer periphery of the secondary section is configured to face the slit while remaining within the first functional unit with or without at least a section of the outer periphery of the secondary section being flush with the slit; and
in the second position, the outer periphery of the primary section is configured to protrude out of the slit and the outer periphery of the secondary section and/or peripheral gap is configured to remain within the first functional unit.

11. The hearing aid according to claim 9, wherein the moveable element is coupled to an actuator, at least partly comprised in the first functional unit and accessible from outside a body of the first functional unit, the actuator being configured to move the moveable element between the first position and the second position.

12. The hearing aid according to claim 11, wherein the first functional unit comprises a slit configured to allow the part of the moveable element to protrude out of the first functional unit in response to an actuation force applied to the actuator.

13. The hearing aid according to claim 12, further comprising a friction element arranged within the first functional unit, the friction element being configured to cooperate with the moveable element and/or actuator such that the moveable element moves between the first position and the second position in response to the actuation force that is above a friction threshold, which is defined by the friction between the friction element and moveable element and/or actuator.

14. The hearing aid according to claim 11, wherein
the moveable element comprises a rotatable unit configured to rotate around a rotation axis; and
the actuator comprises a rotatable actuator configured to rotate around the rotation axis, the rotation of the actuator is configured to rotate the rotatable unit around the rotation axis between the first position and second position.

15. A hearing aid comprising
a first functional unit;
a second functional unit configured to removably couple with the first functional unit, the coupling being configured to provide at least a mechanical connection between the first functional unit and the second functional unit; wherein
the first functional unit comprises a moveable element that is configured to move between a first position and a second position such that in the first position, the moveable element is contained entirely within the first functional unit and in the second position, a part of the moveable element is configured to protrude out of the first functional unit,
the second functional unit comprises a recess configured to receive the part of the moveable element that protrudes out of the first functional unit such that the first functional unit and the second functional unit are immovably locked with respect to each other in response to the moveable element is received in the recess, wherein
the first functional unit comprises a first pair of at least substantially parallel sides, each comprising a first guide channel defined by a first gap between a pair of extension portions of the side;
the second functional unit comprises a second pair of at least substantially parallel sides, each comprising a second guide channel defined by a second gap between the second surface and a second extension portion of the side; and
one of the pair of extension portions is adapted to slide between a second receiving edge of the second surface though the second guide channel to a second terminating end of the second surface and the second extension portion is adapted to slide between a first receiving edge of the first surface though the first guide channel to a first terminating end of the first surface.

16. The hearing aid according to claim 15, wherein
the first gap is configured to decrease in a first gap width starting from a first receiving edge to a first terminating end, and the second gap is configured to decrease in a second gap width starting from a second receiving edge to a second terminating end; and
one of the extension member of the pair of extension portion of the side associated with the first functional unit is configured to include a first extension width that is configured to increase starting from a first receiving edge to a first terminating end, and one of the extension member of the pair of extension portion of the side associated with the second functional unit is configured to include a second extension width that is configured to increase starting from a second receiving edge to a second terminating end.

17. The hearing aid according to claim 15, further comprising
at least two electrical pins and at least two electrical slots being configured to receive corresponding of the at least two electrical pins for providing electrical connection between the first functional unit and the second functional unit, wherein the at least two electrical pins and at least two electrical slots are positioned respectively adjacent to one of a) the first terminating end and second receiving edge, or b) the first receiving edge and second terminating end, or c) the second terminating end and first receiving edge, or d) second receiving edge and first terminating end; and
an alignment structure comprising at least one elongated paths provided around the at least two electrical pins and/or at least two electrical slots, wherein
the at least one elongated path is configured to orient the at least two electrical pins in alignment with the at least two electrical slots and/or to orient the at least two electrical slots in alignment with the at least two electrical pins such that each of the at least two electrical pins is received in the corresponding one of the at least two electrical slots.

18. The hearing aid according to claim 15, further comprising
at least two electrical pins and at least two electrical slots, the at least two electrical pins and at least two electrical slots being positioned respectively adjacent to one of a) the first terminating end and second receiving edge, or b) the first receiving edge and second terminating end, or c) the second terminating end and first receiving edge, or d) second receiving edge and first terminating end; and
at least one of a pin region or a slot region comprises at least one capillary stop, the pin region being defined by a space provided between the at least two electrical pins and the slot region being defined by a space provided between the at least two electrical slots.

19. The hearing aid according to claim 12,
wherein the moveable element is coupled to an actuator, at least partly comprised in the first functional unit and accessible from outside a body of the first functional unit, the actuator being configured to move the moveable element between the first position and the second position,
wherein the first functional unit comprises a slit configured to allow the part of the moveable element to protrude out of the first functional unit in response to an actuation force applied to the actuator,
further comprising a friction element arranged within the first functional unit, the friction element being configured to cooperate with the moveable element and/or actuator such that the moveable element moves between the first position and the second position in response to the actuation force that is above a friction threshold, which is defined by the friction between the friction element and moveable element and/or actuator.

* * * * *